US006043378A

United States Patent [19]

Begley et al.

[11] Patent Number: 6,043,378

[45] Date of Patent: Mar. 28, 2000

[54] PHOTOGRAPHIC ELEMENTS CONTAINING DEVELOPMENT INHIBITOR RELEASING COMPOUNDS

[75] Inventors: William James Begley, Webster; Frank D. Coms, Fairport; Daniel L. Kapp, Rochester, all of N.Y.

[73] Assignee: Eastman Kodak Company, Rochester, N.Y.

[21] Appl. No.: 09/036,066

[22] Filed: Mar. 6, 1998

Related U.S. Application Data

[62] Division of application No. 08/732,572, Oct. 17, 1996, Pat. No. 5,759,757.

[51] Int. Cl.[7] .................. C07D 403/04

[52] U.S. Cl. .................. 548/255; 548/257; 548/261

[58] Field of Search .................. 548/255, 257, 548/261

[56] References Cited

U.S. PATENT DOCUMENTS

| | | | |
|---|---|---|---|
| 3,617,291 | 11/1971 | Sawdey | 430/544 |
| 4,870,000 | 9/1989 | Bergthaller et al. | 430/505 |
| 5,021,330 | 6/1991 | Bergthaller et al. | 430/544 |
| 5,021,331 | 6/1991 | Vetter et al. | 430/544 |
| 5,021,332 | 6/1991 | Bergthaller et al. | 430/544 |
| 5,035,987 | 7/1991 | Odenwalder et al. | 430/544 |
| 5,169,749 | 12/1992 | Katoh et al. | 430/548 |
| 5,200,306 | 4/1993 | Odenwalder et al. | 430/505 |
| 5,270,157 | 12/1993 | Bell et al. | 430/505 |
| 5,298,383 | 3/1994 | Mihayashi et al. | 430/557 |
| 5,306,607 | 4/1994 | Begley et al. | 430/544 |
| 5,310,642 | 5/1994 | Vargas et al. | 430/544 |
| 5,334,490 | 8/1994 | Begley | 430/382 |
| 5,352,570 | 10/1994 | Begley | 430/544 |
| 5,354,650 | 10/1994 | Southby et al. | 430/544 |
| 5,358,828 | 10/1994 | Begley et al. | 430/385 |
| 5,360,709 | 11/1994 | Ohkawa et al. | 430/544 |
| 5,362,880 | 11/1994 | Begley | 548/257 X |
| 5,380,633 | 1/1995 | Harder et al. | 430/505 |
| 5,451,496 | 9/1995 | Merkel et al. | 430/544 |
| 5,474,886 | 12/1995 | Nakazyo et al. | 430/544 |
| 5,817,809 | 10/1998 | Begley et al. | 548/255 X |

FOREIGN PATENT DOCUMENTS

| | | |
|---|---|---|
| 0 578 167 | 1/1974 | European Pat. Off. . |
| 0 296 784 | 12/1988 | European Pat. Off. . |
| 447 920 | 9/1991 | European Pat. Off. . |
| 501 468 | 9/1992 | European Pat. Off. . |
| 513 496 | 11/1992 | European Pat. Off. . |
| 606 914 | 7/1994 | European Pat. Off. . |
| 837362 | 4/1998 | European Pat. Off. . |
| 3644416 | 7/1988 | Germany . |
| 54-67419 | 5/1979 | Japan . |
| 61-73955 | 4/1986 | Japan . |
| 02-169158 | 7/1987 | Japan . |
| 3-142447 | 6/1991 | Japan . |
| 6-273900 | 9/1994 | Japan . |

OTHER PUBLICATIONS

Chemical Abstracts, Chemical Subject Index, 91 CS 4, 4942CS, 1979.

Iitaka et al., Chemical Abstracts, 91:184919q, 1979.

Patent Abstracts of Japan, vol. 012, No. 406(P–777), Oct. 27, 1988 & JP 63 144353 A, Jun. 16, 1988.

Patent Abstracts of Japan, vol. 010, No. 243 (P–489), Aug. 21, 1986 & JP 61 073955 A, Apr. 16, 1986.

Patent Abstracts of Japan, vol. 017, No. 341 (P–1565), Jun. 28, 1993 & JP 05 045813 A, Feb. 26, 1993.

*Primary Examiner*—Fiona T. Powers
*Attorney, Agent, or Firm*—Sarah Meeks Roberts

[57] ABSTRACT

A photographic element comprising a support having situated thereon at least one silver halide emulsion layer, the element containing an image modifying compound which comprises a magenta coupler moiety which upon reaction with oxidized color developing agent during processing forms a dye, said coupler moiety having attached to the coupling site, either directly or through a timing group, a 1,2,3-triazole moiety, the attachment being through the second nitrogen atom of the triazole moiety.

2 Claims, No Drawings

PHOTOGRAPHIC ELEMENTS CONTAINING DEVELOPMENT INHIBITOR RELEASING COMPOUNDS

CROSS REFERENCE TO RELATED APPLICATION

This is a Divisional of application Ser. No. 08/732,572, filed Oct. 17, 1996 now U.S. Pat. No. 5,759,757.

FIELD OF THE INVENTION

This invention relates to development inhibitor releasing compounds and silver halide photographic elements containing such compounds.

BACKGROUND OF THE INVENTION

Various ways are recognized in the photographic industry for releasing a photographic inhibitor from a compound, such as a coupler, in a photographic silver halide material and process. Release can be indirect through a linking or timing group or it can be direct, for example, upon reaction of the coupler with oxidized color developing agent during processing. Image-modifying couplers that release photographic inhibitors directly from the coupler are preferred in the photographic industry because manufacturing such couplers is easier, faster and less costly. However, many times direct release couplers, due to their inflexibility with regard to timing of release, are not practical for and effective at providing desired effects such as reduction of gradation, production of a finer color grain, improvement of sharpness through the so-called edge effect and improvement of color purity and color brilliance through inter-image effects. In this connection, reference is made to the article by C. R. Barr, J. R. Thirtle and P. W. Vittum entitled "Development-Inhibitor-Releasing (DIR) Couplers in Color Photography" in Photographic Science and Engineering 13, 74(1969).

The problem of timing of release has been addressed through the use of timing groups such as described in U.S. Pat. Nos. 4,248,962, 4,409,323 and 4,861,701. European Patent Applications 0 499 279 and 0 438 129 describe photographic compounds having a heterocyclic timing nucleus attached to a coupler moiety through an —O—C(O)— or —$OCH_2$— group, or other group capable of releasing the heterocyclic timing nucleus by electron transfer down an unconjugated chain. However, the use of timing groups can create other problems. For example, many couplers have little flexibility in their rate of release of a PUG, or in their synthetic design, as they are limited by the presence of a particular first timing or linking group, particularly with regard to substituents on such groups. More importantly, though, some couplers exhibit poor stability when stored for prolonged periods under tropical conditions. Thus, they are of limited practical value in today's photographic industry.

Triazoles have been described for use as development inhibitors and have been utilzed in DIR couplers, see for example U.S. Pat. Nos. 5,200,306, 5,360,709, 5,306,607, 5,380,633 and 5,270,157. However, the particularly useful compounds of this invention have not been utilized or suggested.

Therefore, a need has existed for a photographic coupler that is synthetically simple to manufacture; has the flexibility to work in a variety of situations; and that is stable when stored for prolonged periods, especially under tropical conditions. The coupler should be capable of releasing a development inhibitor, thereby providing interlayer interimage effects and increased acutance for the image produced upon processing photographic material containing the coupler.

SUMMARY OF THE INVENTION

This invention provides a photographic element comprising a support having situated thereon at least one silver halide emulsion layer, the element containing an image modifying compound which comprises a magenta coupler moiety which upon reaction with oxidized color developing agent during processing forms a dye, said coupler moiety having attached to the coupling site, either directly or through a timing group, a 1,2,3-triazole moiety, the attachment being through the second nitrogen atom of the triazole moiety.

This invention also provides a process of forming an image in an exposed photographic silver halide element containing an image modifying compound as described above comprising developing the element with a color photographic silver halide developing agent. This invention also provides compounds as described above.

The image modifying compounds utilized in this invention provide improved interlayer interimage effects and acutance levels in the photographic elements in which they are contained. The new compounds are synthetically simple to manufacture and are much more stable than previously known photographic inhibitor releasing couplers containing a 1,2,3-triazole moiety. Further, the image modifying compounds are capable of and more preferably utilize direct release of 1,2,3-triazole inhibitors and they provide a wide range of reactivities depending upon the particular selection of the 1,2,3-triazole inhibitor and the substituents thereon. These compounds, unlike many other untimed or unlinked DIR couplers, can deliver a development inhibitor at a distance from the point at which oxidized color developing agent reacted with the coupler.

DETAILED DESCRIPTION OF THE INVENTION

The image modifying compounds of this invention comprise a magenta coupler moiety, more preferably a pyrazalone coupler moiety, and a 1,2,3-triazole moiety wherein the triazole moiety is attached to the coupling site of the magenta coupler moiety via N-2, the second nitrogen atom of the 1,2,3-triazole ring. Suitable magenta couplers are described in such representative patents and publications as U.S. Pat. Nos. 2,311,082, 2,343,703, 2,369,489, 2,600,788, 2,908,573, 3,062,653, 3,152,896, 3,519,429, 3,758,309, 4,540,654, and "Farbkuppler-eine Literature Ubersicht," published in Agfa Mitteilungen, Band III, pp. 126–156 (1961).

While one of the main advantages of the image modifying compounds is that the coupler may be directly attached to the 1,2,3-triazole moiety, making the use of a timing or linking group unnecessary, an indirect attachment through a timing or linking group may be utilized. More preferably the attachment is direct.

In the image modifying compound the coupler moiety is ballasted if no timing or linking group is utilized. If a timing or linking group is utilized the ballast optionally may be attached to such a group or the coupler moiety. The compound can be monomeric, or it can be a dimeric, oligomeric or polymeric image modifying compound, in which case it may contain more than one 1,2,3-triazole moiety. The image modifying compound can also be a bis compound in which the 1,2,3-triazole moiety forms part of a link between two coupler moieties.

In one suitable embodiment the image modifying compound is represented by the following formula.

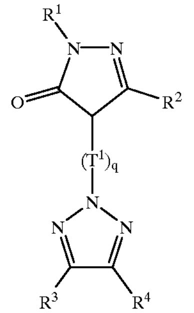

$R^1$ and $R^2$ are independently selected from hydrogen, or an aliphatic, carbocyclic, heterocyclic, carbamoyl, sulfamoyl, carbonamido, sulfonamido, alkoxycarbonyl, nitro, cyano, amino, alkoxy, alkoxyalkyl, aryloxy, aryloxyalkyl, thioalkoxy, thioalkoxyalkyl, thioaryloxy, thioaryloxyalkyl, alkyl- or arylketo, alkyl or arylsulfo group.

$R^3$ and $R^4$ are independently selected from an aliphatic, carbocyclic, or heterocyclic group; a halide atom, or a hydroxy, acyl, alkyl or aryl sulfo, nitro, cyano, amino, alkyl- or arylketo, alkoxy, alkoxyalkyl, aryloxy, aryloxyalkyl, thioalkoxy, thioalkoxyalkyl, thioaryloxy, thioaryloxyalkyl, alkoxycarbonyl, aryloxycarbonyl, carbamoyl, carbonamido, or sulfonamido group, or $R^3$ and $R^4$ may be bonded together to form a 5, 6 or 7 membered heterocyclic or carbocyclic ring, preferably a heterocyclic or saturated carbocyclic ring. $T^1$ is a timing group. q is 0 or 1, more preferably 0.

Branched or unbranched aliphatic, carbocyclic, or heterocyclic groups and groups suitable for substitution on each of these groups as used herein and elsewhere in this application are defined in accordance with the definitions set forth in Grant and Hackh's *Chemical Dictionary*, fifth ed., McGraw-Hill 1987, and in accordance with general rules of chemical nomenclature.

Exemplary aliphatic groups include alkyl, alkene, and alkyne groups, particularly those having 1 to 25 carbon atoms. Examples of useful groups include methyl, ethyl, pr6pyl, butyl, pentyl, hexyl, octyl, nonyl, decyl, dodecyl, pentadecyl, hexadecyl, octadecyl, isopropyl, iso-butyl, sec-butyl, t-butyl, butenyl, iso-pentyl, sec-pentyl, tert-pentyl, pentenyl, hexenyl, octenyl, dodecenyl, propynyl, butynyl, pentynyl, hexynyl, and octynyl.

Exemplary carbocyclic groups (which include aryl groups) are those having a cyclic portion of 4 to 10 carbon atoms. Examples of useful groups include phenyl, tolyl, naphthyl, cyclohexyl, cyclopentyl, cyclohexenyl, cycloheptatrienyl, cyclooctatrienyl, cyclononatrienyl, cyclopentenyl, anilinyl, and anisidinyl.

Exemplary heterocyclic groups (which include heteroaryl groups) are those in which the cyclic portion has 5 to 10 atoms. Examples of useful groups include pyrrolyl, furyl, tetrahydrofuryl, pyridyl, picolinyl, piperidinyl, morpholinyl, thiadiazolyl, thiatriazolyl, benzothiazolyl, benzoxazolyl, benzimidazolyl, benzoselenozolyl, indazolyl, quinolyl, quinaldinyl, pyrrolidinyl, thiophenyl, oxazolyl, thiazolyl, imidazolyl, selenazolyl, tellurazolyl, triazolyl, tetrazolyl, oxadiazolyl, thienyl, pryanyl, chromenyl, isothiazolyl, isoxazolyl, pyrazinyl, pyrimidinyl, pyridazinyl, indolyl, purinyl, isoquinolyl, quinoxalinyl, and quinazolinyl. Preferred heteroatoms are nitrogen, oxygen, and sulfur.

It is understood throughout this specification and claims that any reference to a substituent by the identification of a group or a ring containing a substitutable hydrogen (e.g., alkyl, amine, aryl, alkoxy, heterocyclic, etc.), unless otherwise specifically described as being unsubstituted or as being substituted with only certain substituents, shall encompass not only the substituent's unsubstituted form but also its form substituted with any substituents which do not negate the advantages of this invention. The term lower alkyl used herein means 1 to 5 carbon atoms. The term carbocyclic or heterocyclic group or ring, unless otherwise indicated, includes bicyclic or other fused rings. Also, reference to the term heterocyclic groups includes attachment at any position on the heterocycle.

Groups suitable for substitution, which may themselves be substituted, include, but are not limited to, alkyl groups (for example, methyl, ethyl, hexyl), fluoroalkyl groups (for example, trifluoromethyl), alkoxy groups (for example, methoxy, ethoxy, octyloxy), aryl groups (for example, phenyl, naphthyl, tolyl), hydroxy groups, halogen groups, aryloxy groups (for example, phenoxy), alkylthio groups (for example, methylthio, butylthio), arylthio groups (for example, phenylthio), acyl groups (for example, acetyl, propionyl, butyryl, valeryl), sulfonyl groups (for example, $RSO_2$—, methylsulfonyl, phenylsulfonyl), acylamino groups (for example, RCONH—), sulfonylamino groups (for example, $RSO_2NH$—), carbamoyl groups (for example, RNHCO—, N-methylcarbamoyl), sulfamoyl groups (for example, $RNHSO_2$—, N-phenylsulfamoyl), acyloxy groups (for example, $RCO_2$-acetoxy, benzoxy), carboxy groups, alkoxycarbonyl, aryloxycarbonyl, and heteroxycarbonyl groups (for example, —$CO_2R$), carbamate groups (for example, —$NHCO_2R$, N-methyl phenyl carbamate), ureido groups, cyano groups, sulfo groups, and amino groups.

In one embodiment $R^1$ and $R^2$ are selected from a branched or unbranched aliphatic group, a carbocyclic, or heterocyclic group and at least one of $R^1$ or $R^2$ contains a photographic ballast group. Preferably $R^1$ is a carbocyclic or heterocyclic group, and $R^2$ is a branched or unbranched aliphatic group.

In one preferred embodiment $R^1$ is represented by the following formula.

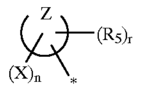

* point of attachment to coupler moiety

Z contains the atoms necessary to complete a heterocyclic ring which in turn may be fused with another ring. Examples of suitable heterocyclic rings include pyridine, furan, indole, thiophene, quinoline, isoquinoline, pyrrole, indole, pyrazole, indazole, imidazole, benzimidazole, 1,2,3-triazole, 1,2,4-triazole, and benzotriazole.

X is independently selected from a hydrogen, chlorine, bromine, or fluorine atom, or a carbamoyl, sulfamoyl, carbonamido, sulfonamido, alkoxycarbonyl, alkyl or aryl keto, alkyl or aryl sulfo, nitro, cyano, amino, alkoxy, alkoxyalkyl, aryloxy, aryloxyalkyl, thioalkoxy, thioalkoxyalkyl, thioaryloxy, or thioaryloxyalkyl group. Preferably X is a chlorine atom or a sulfamoyl, carbonamido, sulfonamido or alkoxy group.

$R^5$ is a photographic ballast group which preferably contains 1 to 40 carbon atoms, and more preferably 1 to 25 carbon atoms. r is 0 or 1, more preferably 1. n is selected from 0, 1, 2, 3, 4 or 5, more preferably n is 0, 1, 2, or 3.

In another embodiment $R^1$ is represented by the formula

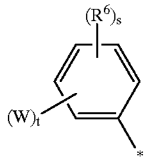

* point of attachment to coupler moiety

W is independently selected from a hydrogen, chlorine, bromine, or fluorine atom or a carbamoyl, sulfamoyl, carbonamido, sulfonamido, alkoxycarbonyl, alkyl or aryl keto, alkyl or aryl sulfo, nitro, cyano, amino, alkoxy, alkoxyalkyl, aryloxy, aryloxyalkyl, Asthioalkoxy, thioalkoxyalkyl, thioaryloxy, or thioaryloxyalkyl group. $R^6$ is a photographic ballast which preferably contains 1 to 40 carbon atoms, and more preferably contains 1 to 25 carbon atoms. s is 0 or 1, preferably 1 and t is selected from 0, 1, 2 3 4, or 5 and more preferably t is 0, 1, 2 or 3.

In one suitable embodiment $R^3$ is ** —$C_mH_{2m+1}$ or 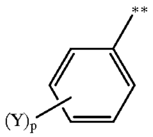

point of attachment to triazole moiety and $R^4$ is  —$CO_2R^7$ wherein $R^7$ is a branched or unbranched aliphatic group, carbocyclic, or heterocyclic group; and m is an integer selected from 1 through 10. $R^7$ is preferably an alkyl group having 1 to 10 carbon atoms, a carbocylic group having up to 10 carbon atoms or a heterocyclic group having 5 to 10 carbon atoms.

Y is a substituent independently selected from hydrogen, chlorine, bromine, fluorine atom or a carbamoyl, sulfamoyl, carbonamido, sulfonamido, alkoxycarbonyl, alkyl- or arylketo, alkyl- or arylsulfo, nitro, cyano, amino, alkoxy, alkoxyalkyl, aryloxy, aryloxyalkyl, thioalkoxy, thioalkoxyalkyl, thioaryloxy, or thioaryloxyalkyl group. p is 0, 1, 2, 3, 4 or 5, more preferably 0, 1, 2, or 3. $R^3$ and $R^4$ as defined above are particularly suitable when $R^1$ is represented by the formula

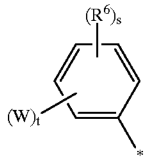

Specific image modifying compounds suitable for use in the invention are as follows:

I-1

Magenta DIR Coupler, I-1:

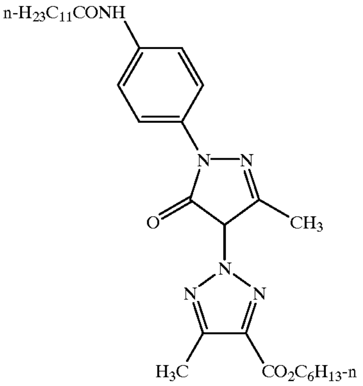

I-2

Magenta DIR Coupler, I-2:

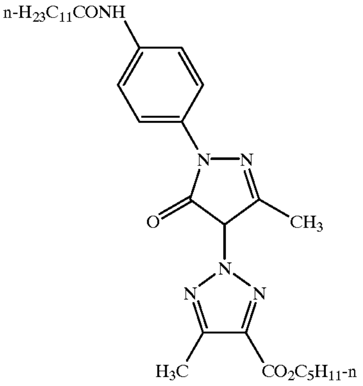

I-3

Magenta DIR Coupler, I-3:

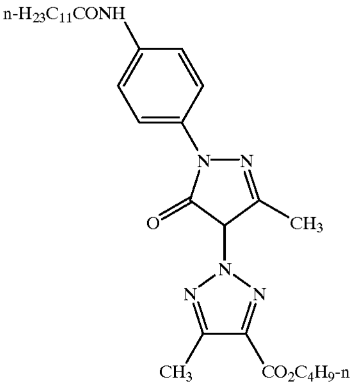

-continued
I-4
Magenta DIR Coupler, I-4:
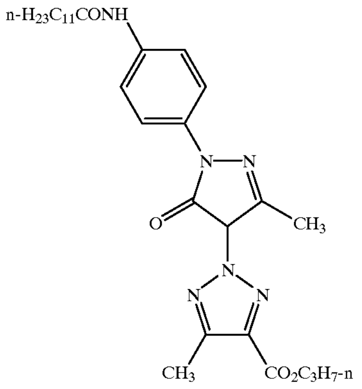
I-5
Magenta DIR Coupler, I-5:
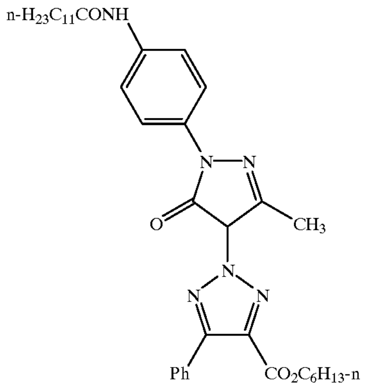
I-6
Magenta DIR Coupler, I-6:
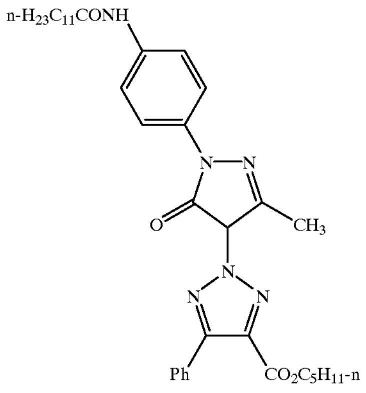
-continued
I-7
Magenta DIR Coupler, I-7:
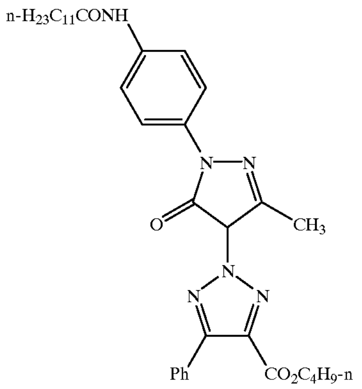
I-8
Magenta DIR Coupler, I-8:
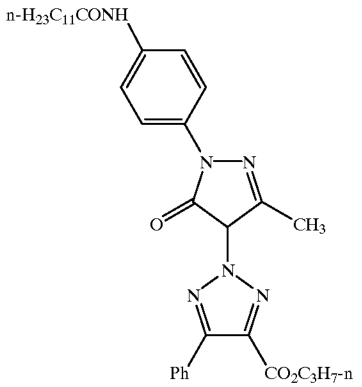
I-9
Magenta DIR Coupler, I-9:
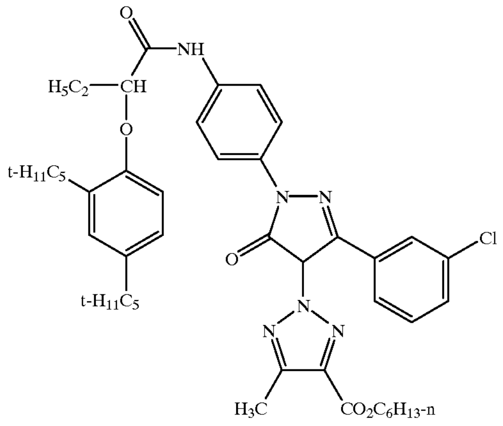

-continued
I-10
Magenta DIR Coupler, I-10:
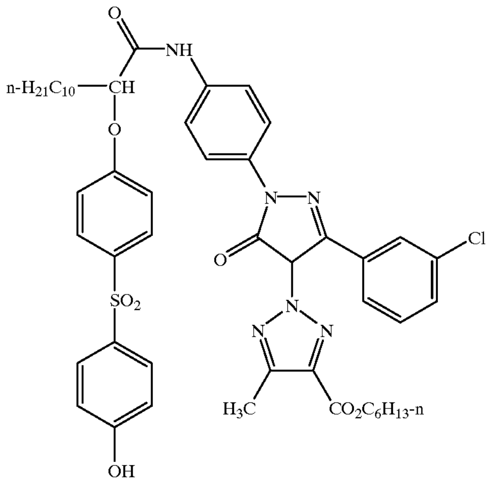
I-11
Magenta DIR Coupler, I-11:
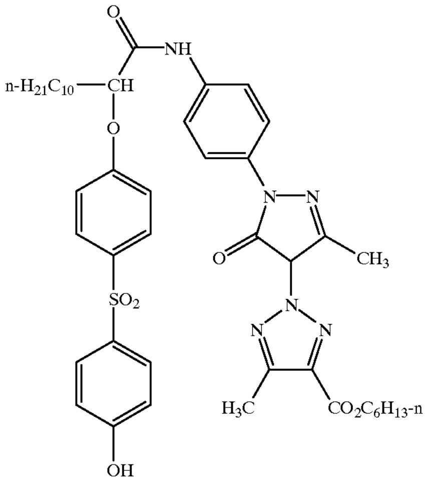
I-12
Magenta DIR Coupler, I-12:
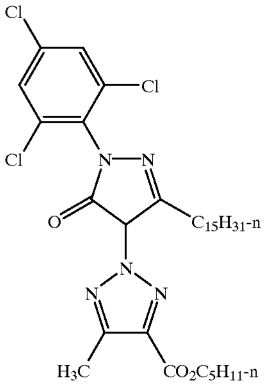
-continued
I-13
Magenta DIR Coupler, I-13:
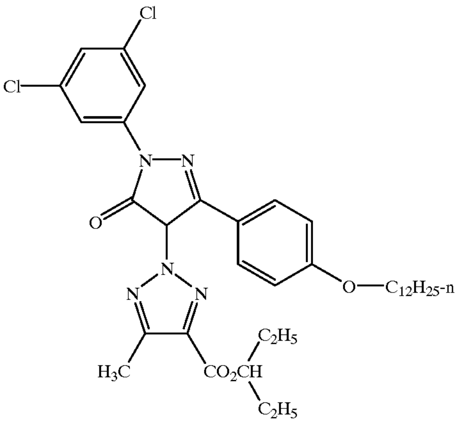
I-14
Magenta DIR Coupler, I-14:
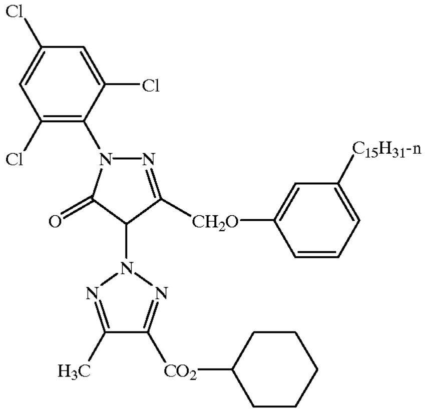
I-15
Magenta DIR Coupler, I-15:
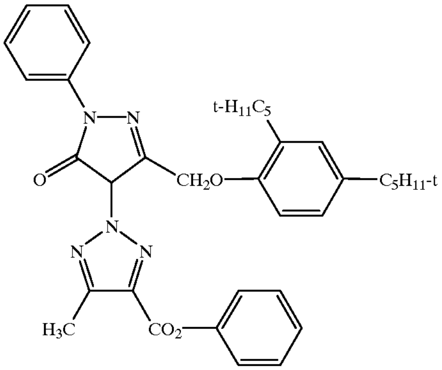

-continued
I-16
Magenta DIR Coupler, I-16:
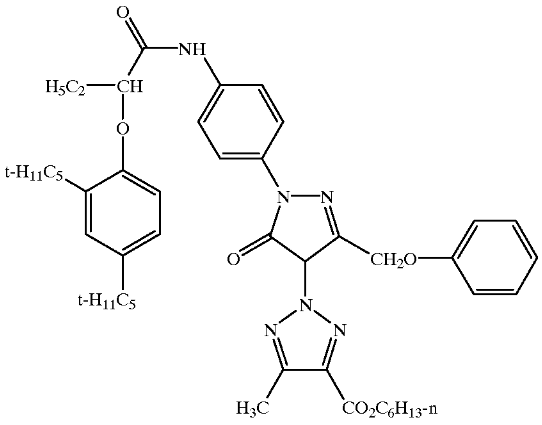
I-17
Magenta DIR Coupler, I-17:
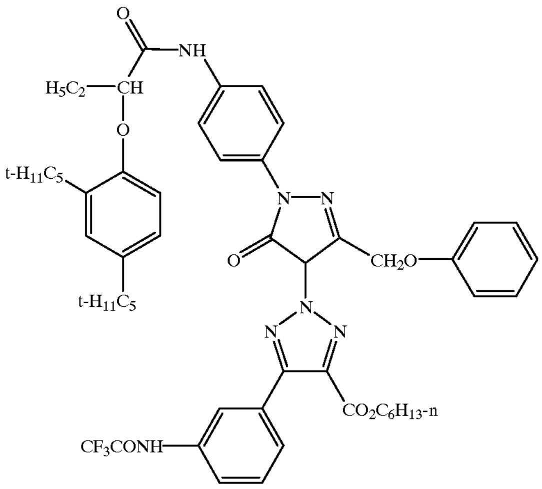
I-18
Magenta DIR Coupler, I-18:
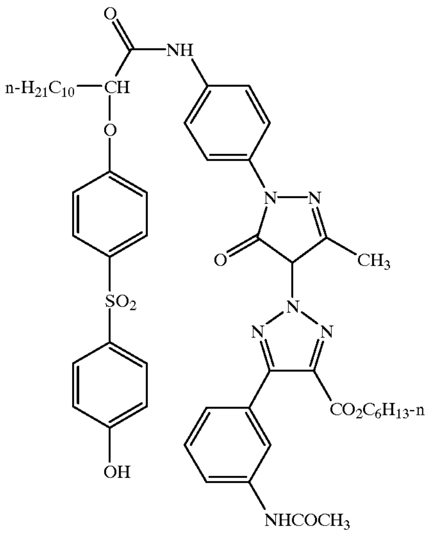
-continued
I-19
Magenta DIR Coupler, I-19:
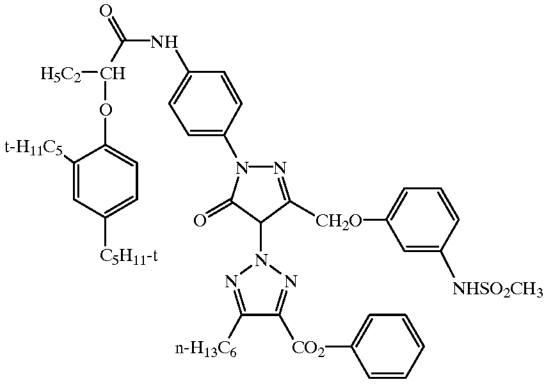
I-20
Magenta DIR Coupler, I-20:
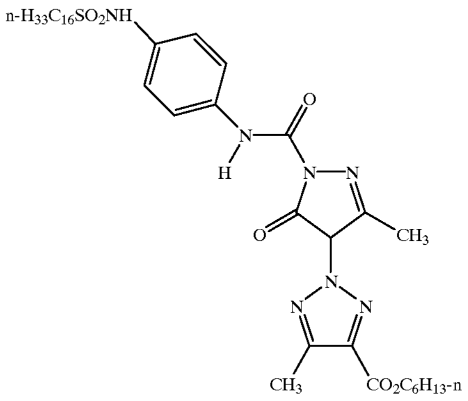
I-21
Magenta DIR Coupler, I-21:
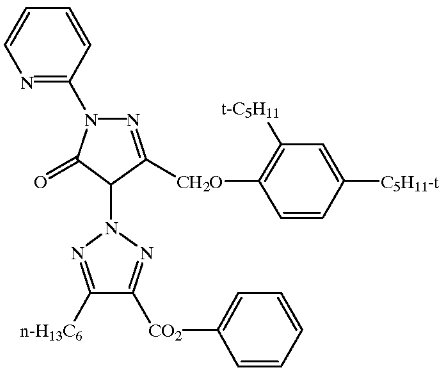

-continued
I-22
Magenta DIR Coupler, I-22:
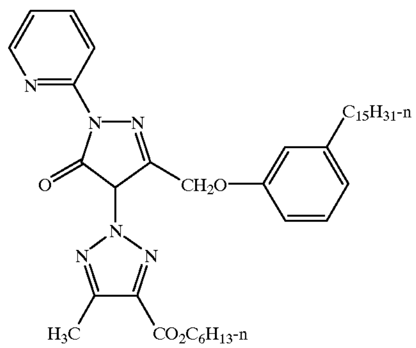
I-23
Magenta DIR Coupler, I-23:
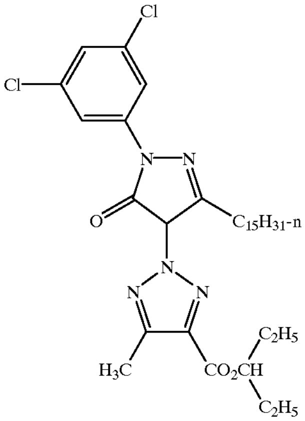
I-24
Magenta DIR Coupler, I-24:
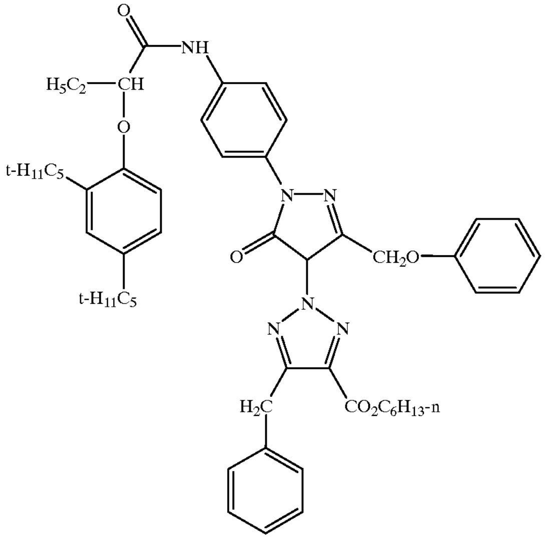
-continued
I-25
Magenta DIR Coupler, I-25:
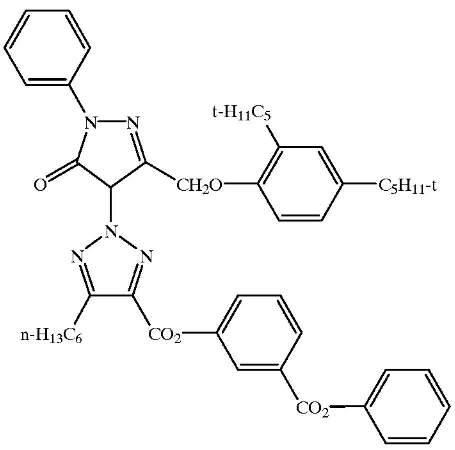
I-26
Magenta DIR Coupler, I-26:
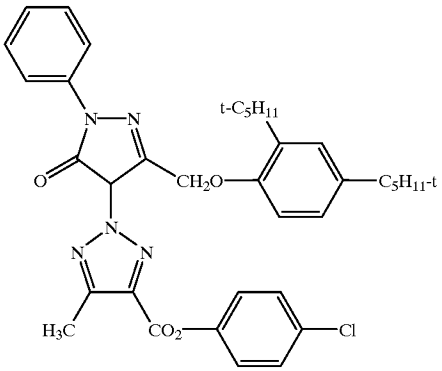
I-27
Magenta DIR Coupler, I-27:
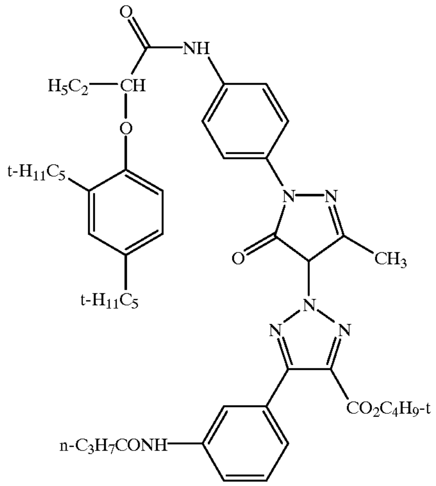

-continued

I-28

Magenta DIR Coupler, I-28:

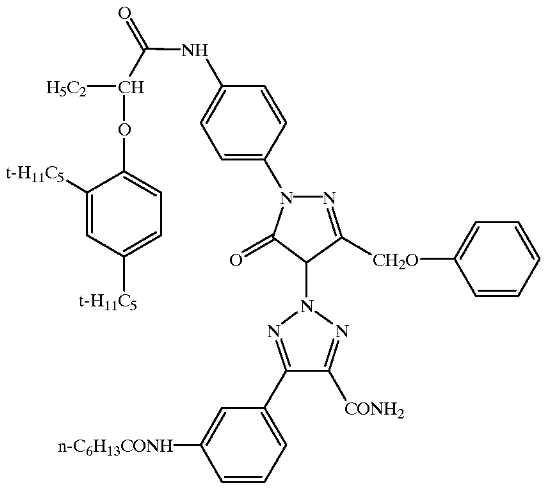

I-29

Magenta DIR Coupler, I-29:

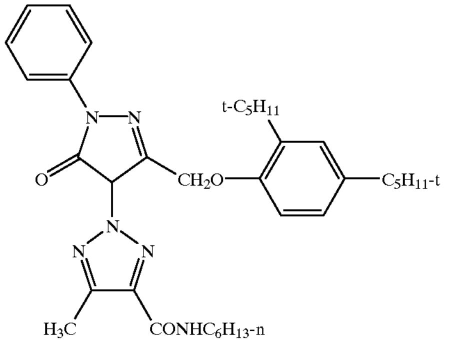

I-30

Magenta DIR Coupler, I-30:

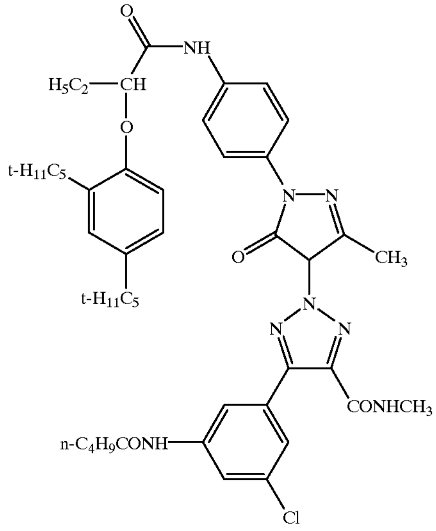

$T^1$, if optionally utilized, can be any timing or linking group known in the art, for instance those described below and in U.S. Pat. Nos. 4,248,962; 4,409,323; 4,421,845; 4,857,447; 4,861,701; 4,864,604; 4,886,736; 4,891,304; 5,034,311; 5,055,385; 5,190,846; and European Patent Application 0 167 168, all of which are incorporated herein by reference. Thus, it may be a timing or linking group which functions by a nucleophilic displacement reaction (of the type described in, for example U.S. Pat. No. 4,248,962) or electron transfer down a conjugated chain (of the type described in, for example, U.S. Pat. No. 4,861,701). It may also be a timing or linking group which functions by electron transfer down an unconjugated chain. These last groups are known in the art under various names. Often they have been referred to as groups capable of utilizing a hemiacetal or iminoketal cleavage reaction or groups capable of utilizing a cleavage reaction due to ester hydrolysis. Regardless of their label, though, their mechanism is that of electron transfer down an unconjugated chain which results, typically, in a relatively fast decomposition and the production of carbon dioxide, formaldehyde or other low molecular weight by-products. Such groups are exemplified specifically in European Patent Application 0 464 612 and 0 523 451, both of which are incorporated herein by reference.

The image modifying compounds can be incorporated in photographic elements by means and processes known in the photographic art. Photographic elements in which the image modifying compounds are incorporated can be simple elements comprising a support and a single silver halide emulsion layer or multilayer, multicolor elements. The compounds can be incorporated in at least one of the silver halide emulsion layers, in particular a green sensitive layer. The compounds may also be incorporated in a non-imaging layer or interlayer. The compounds may be contained in more than one layer, including in both imaging and non-imaging layers. In one embodiment the compounds are contained in an interlayer between a green sensitive layer and another green or non-green sensitive layer, such as an adjacent layer, where they will come into reactive association with oxidized color developing agent which has developed silver halide in the emulsion layer.

The silver halide emulsion layer can contain or have associated with it other photographic couplers such as development inhibitor releasing couplers, including anchimerically assisted development inhibitor releasing couplers, development agent releasing couplers, bleach inhibitor releasing couplers, electron transfer agent releasing couplers, development inhibiting redox releasing couplers, bleach accelerating releasing couplers, dye-forming couplers, colored masking couplers, and/or competing couplers. These other photographic couplers can form dyes of any color and hue or dyes which can wash out of the element during processing. Additionally, the silver halide emulsion layers and other layers of the photographic element can contain addenda conventionally contained in such layers.

A typical multilayer, multicolor photographic element can comprise, preferably in the following order, a support having thereon a red-sensitive silver halide emulsion unit having associated therewith a cyan image dye forming coupler, a green-sensitive silver halide emulsion unit having associated therewith a magenta image dye forming coupler and a blue-sensitive silver halide emulsion unit having associated therewith a yellow image dye forming coupler, at least one of the silver halide emulsion units or another layer having associated therewith an image modifying compound as described above. Each silver halide emulsion unit can be composed of one or more layers and the various units and layers can be arranged in different locations with respect to one another.

The magenta dye image-forming couplers which may be associated with the green-sensitive silver halide emulsion layer are described in such representative patents and publications as; U.S. Pat. Nos. 2,311,082, 2,343,703, 2,369,489, 2,600,788, 2,908,573, 3,062,653, 3,152,896, 3,519,429, 3,758,309, 4,540,654, and "Farbkuppler-eine Literature Ubersicht," published in Agfa Mitteilungen, Band III, pp. 126–156 (1961). Preferably such couplers are pyrazolones, pyrazolotriazoles, or pyrazolobenzimidazoles that form magenta dyes upon reaction with oxidized color developing agents.

The silver halide emulsions can contain grains of any size and morphology. Thus, the grains may take the form of cubes, octahedrons, cubo-octahedrons, or any of the other naturally occurring morphologies of cubic lattice type silver halide grains. Further, the grains may be irregular such as spherical grains or tabular grains. The light sensitive silver halide emulsions can include coarse, regular or fine grain silver halide crystals or mixtures thereof, in a hydrophobic colloid, such as gelatin. The crystals can be comprised of silver chloride, silver bromide, silver bromoiodide, silver chlorobromide, silver chloroiodide, silver chlorobromoiodide and mixtures thereof. The emulsions can be negative-working or positive-working emulsions and can be incorporated into negative or reversal elements as in U.S. Pat. No. 5,411,839, as well as other types of elements known in the art. They can form latent images predominantly on the surface of the silver halide grains or predominantly on the interior of the silver halide grains. They can be chemically and spectrally sensitized by methods known in the art.

The silver halide photographic elements may also contain a transparent magnetic recording layer such as a layer containing magnetic particles on the underside of a transparent support, as described in *Research Disclosure*, November 1992, Item 34390 published by Kenneth Mason Publications, Ltd., Dudley Annex, 12a North Street, Emsworth, Hampshire PO10 7DQ, ENGLAND. Typically, the element will have a total thickness (excluding the support) of from about 5 to about 30 microns. Further, the photographic elements may have an annealed polyethylene naphthalate film base such as described in Hatsumei Kyoukai Koukai Gihou No. 94–6023, published Mar. 15, 1994 (Patent Office of Japan and Library of Congress of Japan) and may be utilized in a small format system, such as described in *Research Disclosure*, June 1994, Item 36230 published by Kenneth Mason Publications, Ltd., Dudley Annex, 12a North Street, Emsworth, Hampshire PO10 7DQ, ENGLAND, and such as the Advanced Photo System, particularly the Kodak ADVANTIX films or cameras.

In the following Table, reference will be made to (1) *Research Disclosure*, December 1978, Item 17643, (2) *Research Disclosure*, December 1989, Item 308119, and (3) *Research Disclosure*, September 1994, Item 36544, all published by Kenneth Mason Publications, Ltd., Dudley Annex, 12a North Street, Emsworth, Hampshire PO10 7DQ, ENGLAND, the disclosures of which are incorporated herein by reference. The Table and the references cited in the Table are to be read as describing particular components suitable for use in the elements of the invention. The Table and its cited references also describe suitable ways of preparing, exposing, processing and manipulating the elements, and the images contained therein. Photographic elements and methods of processing such elements particularly suitable for use with this invention are described in *Research Disclosure*, February 1995, Item 37038, published by Kenneth Mason Publications, Ltd., Dudley Annex, 12a North Street, Emsworth, Hampshire PO10 7DQ, ENGLAND, the disclosure of which is incorporated herein by reference.

| Reference | Section | Subject Matter |
|---|---|---|
| 1 | I, II | Grain composition, |
| 2 | I, II, IX, X, XI, XII, XIV, XV | morphology and preparation. Emulsion preparation including hardeners, coating |
| 3 | I, II, III, IX A & B | aids, addenda, etc. |
| 1 | III, IV | Chemical sensitization and |
| 2 | III, IV | spectral sensitization/ |
| 3 | IV, V | desensitization |
| 1 | V | UV dyes, optical brighteners, |
| 2 | V | luminescent dyes |
| 3 | VI | |
| 1 | VI | Antifoggants and stabilizers |
| 2 | VI | |
| 3 | VII | |
| 1 | VIII | Absorbing and scattering |
| 2 | VIII, XIII, XVI | materials; Antistatic layers; matting agents |
| 3 | VIII, IX C & D | |
| 1 | VII | Image-couplers and image- |
| 2 | VII | modifying couplers; Wash-out |
| 3 | X | couplers; Dye stabilizers and hue modifiers |
| 1 | XVII | Supports |
| 2 | XVII | |
| 3 | XV | |
| 3 | XI | Specific layer arrangements |
| 3 | XII, XIII | Negative working emulsions; Direct positive emulsions |
| 2 | XVIII | Exposure |
| 3 | XVI | |
| 1 | XIX, XX | Chemical processing; |
| 2 | XIX, XX, XXII | Developing agents |
| 3 | XVIII, XIX, XX | |
| 3 | XIV | Scanning and digital processing procedures |

The photographic elements can be incorporated into exposure structures intended for repeated use or exposure structures intended for limited use, variously referred to as single use cameras, lens with film, or photosensitive material package units.

The photographic elements can be exposed with various forms of energy which encompass the ultraviolet, visible, and infrared regions of the electromagnetic spectrum as well as with electron beam, beta radiation, gamma radiation, x-ray, alpha particle, neutron radiation, and other forms of corpuscular and wave-like radiant energy in either noncoherent (random phase) forms or coherent (in phase) forms, as produced by lasers. When the photographic elements are intended to be exposed by x-rays, they can include features found in conventional radiographic elements.

The photographic elements are preferably exposed to actinic radiation, typically in the visible region of the spectrum, to form a latent image, and then processed to form a visible dye image. Development is typically followed by the conventional steps of bleaching, fixing, or bleach-fixing, to remove silver or silver halide, washing, and drying.

The following examples illustrate the practice of the invention. They are intended to be illustrative, and should not be construed as limiting the invention to the specific embodiments disclosed.

EXAMPLES

Synthetic Example

This example can be readily modified by one of ordinary skill in the art to obtain other suitable couplers.

Synthesis of DIR Coupler I-1

Intermediate A-1:

Acetoacetanilide (10.0 g, 56.43 mMole), was dissolved in dry methylene chloride (80 mL) and a solution of sulfuryl chloride (5.03 mL, 62.07 mMole). Dry methylene chloride (20 mL) was added dropwise over a 15 minute period with stirring while maintaining the temperature at approximately 20° C. After a further 15 minutes of stirring at room temperature the solution was concentrated under reduced pressure and treated with dry diethyl ether (100 mL). The precipitated product was filtered off, washed with a little ice cold dry diethyl ether and air dried. This gave 7.5 g of Intermediate A-1.

Intermediate A-2:

Intermediate A-1 (10.0 g, 47.2 mMole), together with n-hexyl 5-methyl-1,2,3-triazole-4-carboxylate (11.0 g, 52.0 mMole) were suspended in dry acetonitrile (100 mL). To this mixture was added tetramethylguanidine (11.8 mL, 94.5 mMole) whereupon dissolution was achieved. This reaction mixture was heated at 50° C. for 1 hour. After this period the reaction mixture was cooled and diluted with ethyl acetate. The ethyl acetate solution was washed with 2N-HCl(×1), dried over $MgSO_4$, filtered, and concentrated to yield an oil. This oil was dissolved in a solvent mix of 15% ethyl acetate in heptane and subjected to medium pressure flash chromatography eluting with the same solvent mixture. The first major component was isolated and concentrated under reduced pressure to yield intermediate A-2, yield 12.5 g.

Intermediate A-3:

Intermediate A-2 (10.0 g, 25.88 mMole) together with p-nitrophenylhydrazine hydrochloride (5.4 g, 28.46 mMole) were suspended in acetic acid (100 mL) with stirring and heated to 80° C. for 1 hour. At the end of this period the solution was cooled and concentrated under reduced pressure. The residue was treated with water (200 mL), and extracted with ethyl acetate while adding a little tetrahydrofuran to aid dissolution. The organic layer was collected, dried over $MgSO_4$, filtered and concentrated. The residue was treated with heptane to give the pyrazolone intermediate A-3. This product was filtered off, washed with heptane and air dried. Yield 9.0 g.

Intermediate A-4:

Intermediate A-3 (5.0 g, 11.67 mMole) was dissolved in 50% tetrahydrofuran-ethyl acetate (100 mL) with slight heating to aid dissolution. Platinium oxide (400 mg) was added and hydrogenation was carried out at 50 psi of hydrogen pressure for 1 hour at room temperature. At the end of this period the hydrogenation was stopped. Without any further workup procedure to isolate intermediate A-4, the resulting mixture was taken on to the next step.

DIR Coupler I-1:

Intermediate A-4 (approximately 11.67 mMole), in the 50% tetrahydrofuran-ethyl acetate solution as described above was stirred at room temperature. To the mixture was added N,N-dimethylaniline (2.96 mL, 23.34 mMole) and then lauroyl chloride (2.7 mL, 11.67 mMole) was added dropwise. After stirring for 15 minutes the reaction mixture was diluted with ethyl acetate and the ethyl acetate was washed with 2N—HCl(×1), brine(×1), dried over $MgSO_4$, filtered over celite and then concentrated under reduced pressure. The resulting oil was dissolved in a mixture of ethyl acetate-methylene chloride-acetic acid in the ratio of 40:160:4 (100 mL) and subjected to medium pressure flash chromatography eluting with the same solvent mixture to elute off impurties and then changed to a ratio of 50:150:4 to obtain the DIR coupler I-1 after solvent removal. The yield of DIR coupler I-1 was 5.0 g.

The above synthesis can be represented by the following scheme:

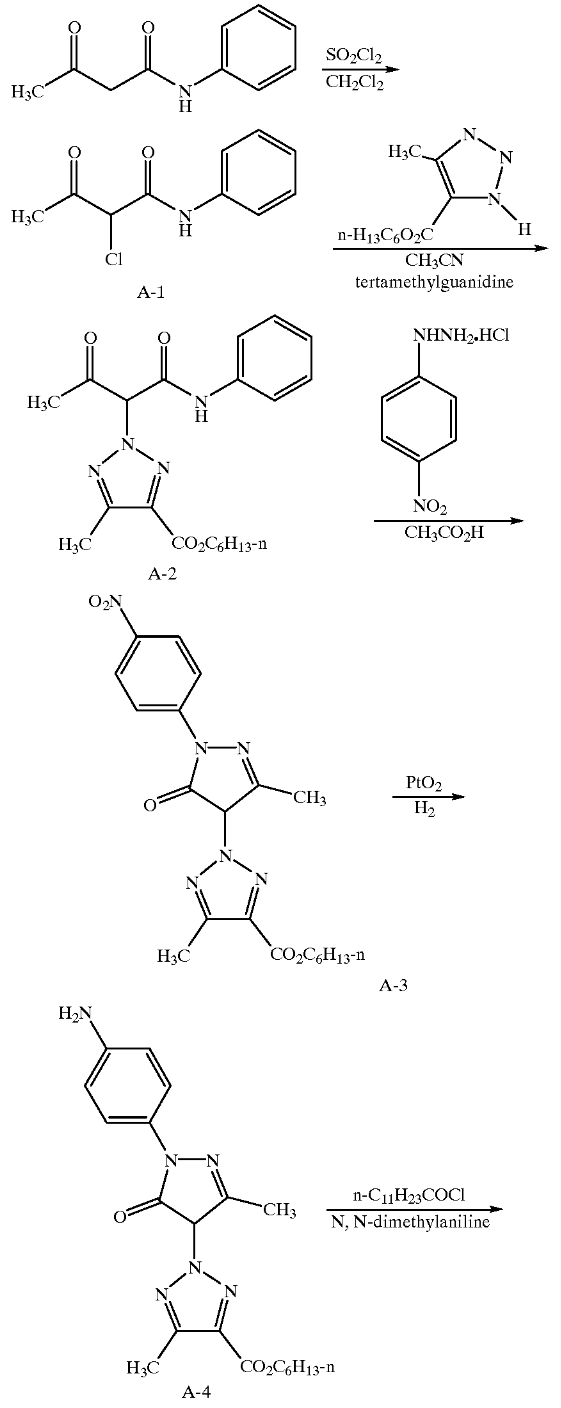

-continued

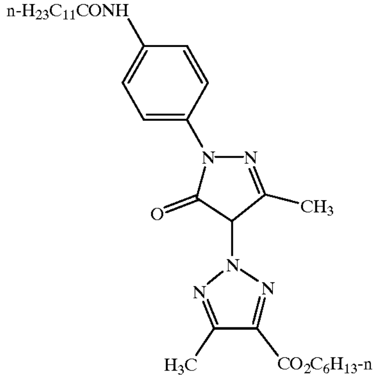

DIR Coupler I-1

Example 1

Photographic elements were prepared by coating the following layers on a cellulose ester film support (amounts of each component are indicated in $mg/m^2$):

Comparative Samples

| | |
|---|---|
| Emulsion layer 1: | Gelatin-(3767); green sensitized silver bromoiodide (as Ag)-(1615); 5-Methyl-1,2,4-Triazolo[1,5-a]pyrimidin-7-o1 sodium salt-(26); Yellow image coupler (Y-1), dispersed in half its weight of coupler solvent S-1,-(699); Yellow DIR coupler dispersed in twice its weight of S-1, see table 1. |
| Protective Overcoat | Gelatin-(2691); Bisvinylsulfonylmethyl ether at 1.75% total gelatin. |

Inventive Samples

| | |
|---|---|
| Emulsion layer 1: | Gelatin-(3767); green sensitized silver bromoiodide (as Ag)-1076); 5-Methyl-1,2,4-Triazolo[1,5-a]pyrimidin-7-o1 sodium salt-(17); Magenta image coupler (M-1), dispersed in an equal weight of a coupler solvent mixture containing 80% S-1, and 20% S-2,-(672); Magenta DIR coupler dispersed in twice its weight of S-1, see table 2. |
| Protective Overcoat | Gelatin-(2691); Bisvinylsulfonylmethyl ether at 1.75% total gelatin. |

Structures of couplers utilized in the above Examples and not previously described are as follows:

Y-1

Yellow Image Coupler, Y-1:

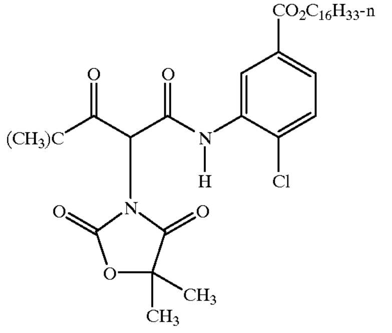

M-1

Magenta Image Coupler, M-1:

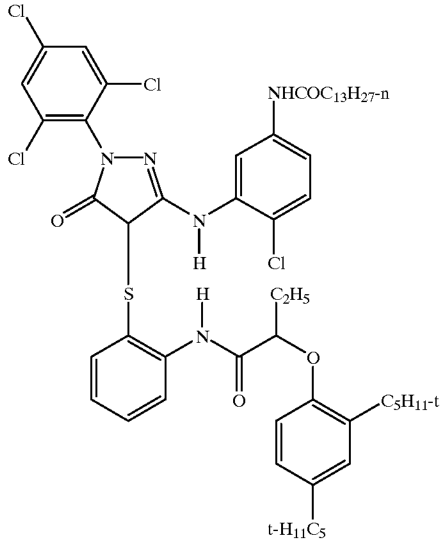

D-1

Yellow DIR Coupler, D-1:

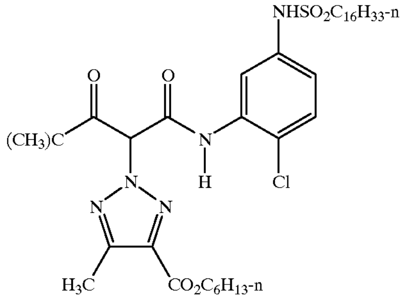

-continued

D-2

Yellow DIR Coupler, D-2:

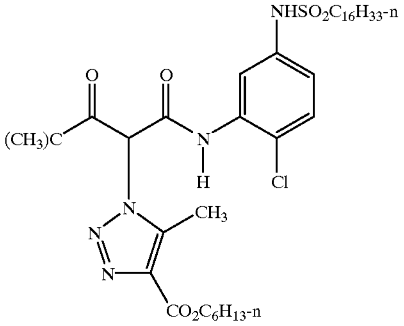

D-3

Yellow DIR Coupler, D-3:

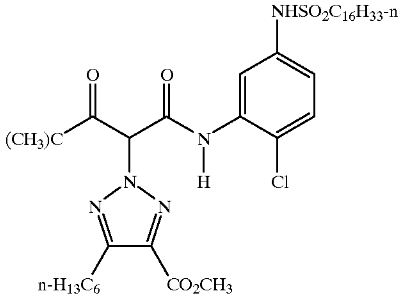

D-4

Yellow DIR Coupler, D-4:

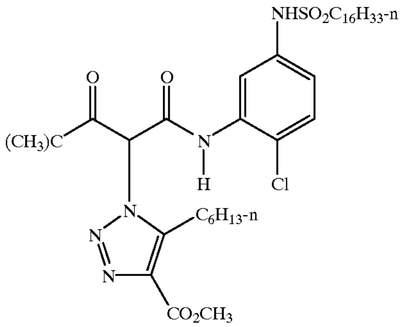

D-5

Magenta DIR Coupler, D-5:

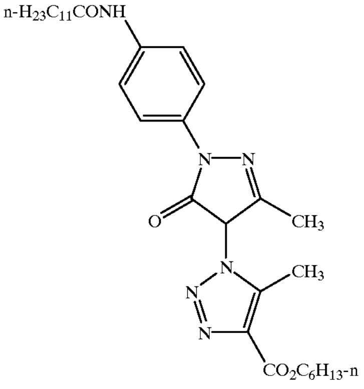

-continued

S-1

Coupler Solvent, S-1:

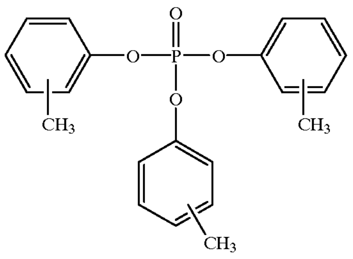

(Mixture of tricresyl phosphates)

S-3

Coupler Solvent, S-2:

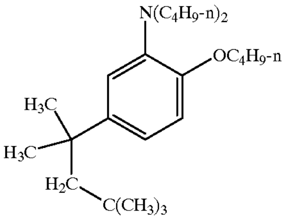

Strips of each sample were exposed to green light through a graduated density step tablet, and then developed for 3.25 minutes at 38° C. in the following color developer. Development was then stopped, and the samples were washed, bleached, fixed, and dried. The processed strips of the comparative samples were read with blue light and those of the inventive samples were read with green light to determine density as a function of exposure and contrast. The photographic and stability results are as shown in tables 1–3.

| Color Developer | |
|---|---|
| Distilled water | 800 mL |
| Sodium Sulfite, anhydrous | 0.38 g |
| CD-4' (color developer)* | 4.52 g |
| Potassium Carbonate, anhyd. | 34.3 g |
| Potassium Bicarbonate | 2.32 g |
| Sodium Bromide | 1.31 g |
| Potassium Iodide | 1.20 mg |
| Hydroxylamine Sulfate | 2.41 g |
| Diethylenetriaminepentacetic acid, pentasodium salt (40% Soln.) | 8.43 g |
| Distilled water | to 1 L |
| Adjust pH to 10.0. | |

*CD-4 ™ is a KODAK color developer in which the active component is 4-amino-3-methyl-N-ethyl-N-beta-hydroxy-ethylaniline sulfate.

TABLE 1

| DIR Coupler | Level ($mg/m^2$) | Gamma ($\gamma$) | Percent $\gamma$ Reduction* |
|---|---|---|---|
| None | 0 | 1.52 | 0 |
| D-1 | 41 | 1.03 | 32 |
| " | 83 | 0.78 | 449 |
| " | 165 | 0.67 | 56 |
| D-2 | 41 | 1.29 | 15 |
| " | 83 | 1.18 | 22 |
| " | 165 | 1.08 | 29 |

TABLE 2

| DIR Coupler | Level ($mg/m^2$) | Gamma (γ) | Percent γ Reduction* |
|---|---|---|---|
| None | 0 | 2.71 | 0 |
| I-1 | 16 | 1.70 | 37 |
| " | 31 | 1.51 | 44 |
| " | 62 | 1.17 | 57 |
| D-5 | 16 | 2.99 | −10 |
| " | 31 | 2.92 | −8 |
| " | 62 | 2.90 | −7 |

*Percent gamma reduction is defined as the (gamma of a non-DIR containing coating minus the gamma of a DIR containing coating) divided by the gamma of the non-DIR containing coating, X 100.

From table 1 it can be seen for a given coating level, coupler D-1 is more effective at reducing gamma when compares to its isomer, coupler D-2. In coupler D-1 the inhibitor is attached to the coupling site of the coupler via the 2-nitrogen of the 1,2,3-triazole ring whereas in coupler D-2 the inhibitor is attached to the coupling site via the 1(3)-nitrogen of the triazole. Because of the effectiveness in reducing gamma in photographic elements, DIR couplers of type D-1 are preferred over their less reactive D-2 isomers.

From table 2 the effectiveness of the isomeric pair of magenta couplers D-5 and I-1 at reducing gamma can be seen. Inventive DIR coupler I-1, which has the 1,2,3-triazole attached to the coupling site via the 2-nitrogen atom, is more effective at reducing gamma than its D-5 isomer, which has the triazole attached to the coupling site via the 1(3)-nitrogen atom.

The stability data for the isomeric DIR coupler pair D-1 and D-2, the isomeric pair D-3 and D-4 and the isomeric pair I-1 and D-5 are shown in table 3 and are expressed as a percentage loss in the DIR coupler.

TABLE 3

| DIR Coupler | Percent Loss |
|---|---|
| D-1 | 34.8 |
| D-2 | 16.3 |
| D-3 | 32.3 |
| D-4 | 18.6 |
| I-1 | 10 |
| D-5 | 11 |

Specifically, percentage loss was determined by extracting the coupler from elements incubated in high temperature and high humidity conditions (4 weeks at 48.9° C. and 50% Relative Humitidy), and comparing the amount of coupler extracted with the amount extracted from similar elements that were not incubated. Extractions were performed by methods known in the art and measurements of coupler amounts were made by HPLC analysis.

It can be seen from table 3 that desirable yellow DIR couplers D-1 and D-3, in which the triazole inhibitor is attached to the coupling site of the coupler via the 2-nitrogen atom, exhibit extremely poor stability when compared to their respective less reactive counterparts D-2 and D-4, which are attached via the 1(3)-nitrogen atom.

However, table 3 shows unexpectedly high stability for magenta DIR coupler I-1, and similar to D-5. Based on the stability difference between isomeric pairs D-1 and D-2, and D-3 and D-4 a similar stability difference would have been expected between I-1 and D-5.

It can be seen from tables 1–3 that the couplers utilized in this invention have superior ability to their check couplers at reducing gamma. Furthermore, couplers of the invention provide unexpectedly high stability when compared to their yellow counterparts.

The invention has been described in detail with particular reference to preferred embodiments thereof, but it will be understood that variations and modifications can be effected within the spirit and scope of the invention.

What is claimed is:

1. A photographic image modifying compound represented by the formula

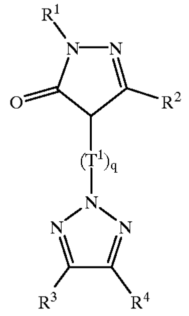

wherein $R^1$ and $R^2$ are independently selected from hydrogen, or an aliphatic, carbocyclic, or heterocyclic group, or the group consisting of carbamoyl, sulfamoyl, carbonamido, sulfonamido, alkoxycarbonyl, aryl- or alkylketo, aryl- or alkylsulfo, nitro, cyano, amino, alkoxy, alkoxyalkyl, aryloxy, aryloxyalkyl, thioalkoxy, thioalkoxyalkyl, thioaryloxy, thioaryloxyalkyl;

$R^3$ and $R^4$ are independently selected from an aliphatic, carbocyclic, or heterocyclic group; a halide atom, or a hydroxy, acyl, aryl- or alkylketo, aryl- or alkylsulfo, nitro, cyano, amino, alkoxy, alkoxyalkyl, aryloxy, aryloxyalkyl, thioalkoxy, thioalkoxyalkyl, thioaryloxy, thioaryloxyalkyl, alkoxycarbonyl, aryloxycarbonyl, carbamoyl, carbonamido, or sulfonamido group;

$T^1$ is a timing group; and q is 0or 1.

2. The photographic image modifying compound of claim 1 wherein $R^1$ and $R^2$ are selected from a branched or unbranched aliphatic group, a carbocyclic, or heterocyclic group and at least one of $R^1$ or $R^2$ contain a photographic ballast.

* * * * *